United States Patent
Minonzio et al.

(10) Patent No.: US 9,121,810 B2
(45) Date of Patent: Sep. 1, 2015

(54) ULTRASONIC METHOD AND DEVICE FOR CHARACTERIZING A MEDIUM

(75) Inventors: Jean-Gabriel Minonzio, Paris (FR); Maryline Talmant, Vermon (FR); Pascal Laugier, Paris (FR)

(73) Assignees: Centre Nationale de la Recherche Scientifique—CNRS, Paris (FR); Université Pierre et Marie Curie (Paris 6), Paris (FR)

( * ) Notice: Subject to any disclaimer, the term of this patent is extended or adjusted under 35 U.S.C. 154(b) by 755 days.

(21) Appl. No.: 13/376,955
(22) PCT Filed: Jun. 11, 2010
(86) PCT No.: PCT/FR2010/051175
§ 371 (c)(1), (2), (4) Date: Jan. 26, 2012
(87) PCT Pub. No.: WO2010/142927
PCT Pub. Date: Dec. 16, 2010

(65) Prior Publication Data
US 2012/0111116 A1 May 10, 2012

(30) Foreign Application Priority Data
Jun. 11, 2009 (FR) .................... 09 02856

(51) Int. Cl.
G01N 29/11 (2006.01)
G01N 29/06 (2006.01)
A61B 8/08 (2006.01)
G01N 29/46 (2006.01)

(52) U.S. Cl.
CPC .......... *G01N 29/0654* (2013.01); *A61B 8/0875* (2013.01); *G01N 29/46* (2013.01); *G01N 2291/02483* (2013.01); *G01N 2291/106* (2013.01)

(58) Field of Classification Search
CPC .............. A61B 2019/5416; A61B 2019/5276; A61B 2019/505; A61B 8/4245; A61B 8/4254; A61B 8/4483; A61B 8/4494; A61B 8/0875; A61B 5/7257; G01N 29/11; G01N 2291/02483; G01B 11/24
USPC ............ 702/159, 19, 108, 124–125, 127, 702/170–171, 189–191, 193, 196; 600/407, 600/437, 443–447; 73/570, 584, 587, 597, 73/645
See application file for complete search history.

(56) References Cited

U.S. PATENT DOCUMENTS
6,449,566 B1 9/2002 Oeschger
2008/0097211 A1 4/2008 Sarvazyan et al.

FOREIGN PATENT DOCUMENTS
WO 03045251 A1 6/2003
WO 03099133 A1 12/2003

OTHER PUBLICATIONS
Sasso et al., Singular Value Decomposition-Based Wave Extraction in Axial Transmission: Application to Cortical Bone Ultrasonic Characterization, Jun. 2008, IEEE Transactions on Ultrasonics, Ferroelectrics, and Frequency Control, vol. 55, No. 6, pp. 1328-1332.*
Pereira et al: "Performance of ultrasound echo decomposition using singular spectrum analysis", Ultrasound in Medicine and Biology, vol. 27, No. 9, Sep. 1, 2001, pp. 1231-1238, XP004308804.
International Search Report, dated Nov. 5, 2010, in Application PCT/FR2010/051175.

* cited by examiner

*Primary Examiner* — Toan Le
(74) *Attorney, Agent, or Firm* — Osha Liang LLP

(57) ABSTRACT

A probe including $N^E$ ultrasonic emitters and $N^R$ ultrasonic receivers is applied on the medium to be characterized. Each emitter is activated successively and each time signals are detected on the set of receivers during a time window. Each of the $N^E \times N^R$ signals detected is converted by temporal Fourier transformation to a sum of vibrational components each having its temporal frequency. For each frequency, a matrix $N^E \times N^R$ of complex amplitudes of vibrational components having this frequency is extracted. These matrices are decomposed into singular values, the smallest are eliminated, and the singular vectors associated with the singular values retained, a base of the space of the reception signals is formed, for each frequency. The contribution of each plane wave, characterized by its velocity, in this base is calculated. This contribution is represented in the form of a grey level in a frequency-propagation velocity reference system.

15 Claims, 9 Drawing Sheets

ULTRASONIC METHOD AND DEVICE FOR CHARACTERIZING A MEDIUM

BACKGROUND

1. Field of the Invention

The present invention relates to an ultrasonic method and an ultrasonic device for characterizing a medium.

The present invention applies in particular to the characterization of solid media constituting objects for which it is a question of ascertaining the nature, composition, degree of homogeneity, state, a dimension etc., in particular by comparison with results established previously for known media.

In particular it may be a matter of detecting the condition of a mechanical component by non-destructive means. More particularly, it may be a question of examining the condition of a human or animal bone, in particular the state of the cortical layer of the bone, for example to ascertain the stage of development of a bone in a child, the condition of a bone in the case of certain disabilities affecting the skeleton, or for detecting bone pathologies such as osteoporosis and if necessary evaluating the severity of the pathology detected.

2. Description of Related Art

Ultrasonic methods offer numerous advantages relative to radiographic methods, which require expensive equipment and a suitable environment, which have undesirable side effects and for which the frequency of application on the same individual must be limited.

Methods of characterization are known that consist of applying ultrasonic excitation at an emission site and detecting, at several successive receiving sites, the arrival of the first signal generated by said excitation, then calculating the velocity of propagation of this first signal. The method can be implemented by applying a probe on the external surface of the patient's body. FR 2 839 877 teaches a method and a device that eliminate the influence of a possibly variable thickness of soft tissues (skin, muscle) between the probe and the bone to be investigated. In the cortical layer of a bone, the velocity of the first signal varies as a function of parameters such as the thickness of the cortical layer, the presence of osteoporosis etc. Just measuring the velocity of the first signal therefore does not always permit discrimination of different symptoms.

SUMMARY

The ultrasonic signal observed at the receivers in response to an excitation such as a pulse or other multifrequency excitation contains several contributions associated with waves that are propagated at different velocities, varying as a function of the frequency, and with different energy levels. Detecting the states of excitation, successive over time, of multiple receivers distributed on the path of the signals, and establishing, based on the result of said detection, an image of the energy levels, as a function of time and space, of the ultrasonic signals transmitted along the medium under investigation, is known. This spatiotemporal image of the energy levels is rich in information as it combines the consequences, in terms of excitation, of the various vibration modes produced by the excitation signal in the medium under investigation. Extraction of a map of the energy levels as a function of the frequency and the velocity of propagation from the signals received by the successive detectors is known. This map takes the form, for example, of a representation, by colour or grey levels, of the energy at each point of a frequency-propagation velocity reference system. Lines of high energy are seen to appear, called "paths", each reflecting a vibration mode and forming a whole that is characteristic of the propagating medium.

In an embodiment that aims to obtain this mapping, the spatiotemporal image can be processed in particular by two-dimensional digital Fourier transformation to extract from it a spectrum of the temporal frequencies and the spatial frequencies, and in particular establish a correspondence between the values of the spatial frequencies and the values of the temporal frequencies. The signals received, sampled over time and, owing to the finite number of receivers, in space, are put into the form of a matrix (time–space) of the energy levels in space and in time. We then perform a two-dimensional digital Fourier transformation (2DFT) of the matrix of energy levels, so as to pass from the variables time and space to the variables frequency and propagation velocity. The aforementioned mapping corresponds to a visualization of the two-dimensional Fourier transform (2DFT).

However, this technique has a certain number of limitations and/or drawbacks. The modes that are weakly energetic tend to be masked by the modes that are more energetic. The quality of the image obtained is degraded in noisy media. Moreover, the known technique requires a large quantity of acquisitions, especially if the number of detectors is limited by the shape or the dimensions of the object incorporating the medium to be characterized. In particular, one technique for improving the performance of the known method consists of performing each measurement a large number of times and then processing mathematically (2DFT) a matrix formed by the mean values of the measurements that were taken. This largely eliminates errors occurring randomly, but not certain sources of systematic errors.

The purpose of the present invention consists of overcoming at least some of the aforementioned drawbacks by proposing a method and/or a device for characterization by ultrasonic means which provides fundamentally better performance than the known technique.

According to the invention, the ultrasonic method of characterization of a medium includes:
  applying an ultrasonic excitation signal to the medium,
  detecting a response constituted by the ultrasonic signals received at several receiving sites located at different distances from an emission site where the excitation signal was applied,
  from the set of ultrasonic signals received, extraction of a map of the modes that have been propagated, in a frequency-propagation velocity reference system,
is characterized in that for each receiving site, detection is performed successively for at least two different excitation signals, so that at least two responses, whose vibrational components are different and/or added differently, pass each receiving site.

It is known that the response to an ultrasonic excitation can be analysed as a summation of vibrational components, each having an amplitude (energy level), a frequency, a position in time (phase), and a propagation velocity.

The excitation (for example a Dirac pulse) can itself be analysed as being formed of vibrational components, each having a frequency and an amplitude (energy level). The excitation is also characterized by the emission site where it is applied, as it is considered in the sense of the invention that two excitation signals are different if they are identically composed but are applied at different emission sites.

A second excitation signal, different from a first excitation signal, generates, in each detector, a response that is different from that generated in this same detector in response to the first excitation signal.

This property can be exploited in various ways. For example, the known method can be carried out several times, by changing the excitation signal from one time to another, each time obtaining the map that corresponds to the excitation signal emitted, then comparing and/or adding the maps obtained to generate a more reliable resultant map.

The invention preferably envisages using more than two different excitation signals, for example about ten, for further improving the basic performance of the invention.

It is preferable according to the invention for the different excitation signals to differ by the distance between their respective emission site and each receiving site. It is also preferable, in this case, for the excitation signals not to have any other difference between them, i.e. for their spectrum of elementary vibrational components to be roughly the same. For example, a Dirac pulse can be used systematically as excitation signal. It is known that the response of an ultrasonic transducer to such a pulse has a spectrum formed from frequencies located in a certain range with a Gaussian distribution of the amplitudes on either side of a central frequency. Since the response to an excitation in a given medium is formed from vibrational components that are propagated at different velocities, the vibrational components of the two responses to two excitation signals that are identically composed but are applied at different distances from a given detector are added differently on passing in front of this detector. The two signals picked up by each detector are therefore different. Once again, more than two different signals can be used, for example about ten signals each applied at a respective emission site.

Thus, in the general case, this preferred version of the method uses $N^E$ emitters and $N^R$ receivers. Preferably, the emitters are activated successively, one at a time, and each time that an emitter is activated, we have acquisition of $N^R$ temporal signals, one on each of the $N^R$ receivers. In total, $N^E \times N^R$ temporal signals are obtained.

In practice, in order to improve detection, each measurement can be performed a predetermined number of times and each aforementioned temporal signal, employed for the rest of the method, can be constituted by the mean value of the signals obtained in response to this predetermined number of identical excitations. This possibility that each temporal signal acquired for the rest of the method is in fact a mean value of several signals actually detected will no longer be mentioned hereinafter, for the sake of clarity.

It is known that any temporal function can be analysed as a sum of sinusoidal functions of time, having an amplitude, a frequency, and a phase (position in time). The amplitude and the phase can be expressed as the module and the argument, respectively, of one and the same complex number, which will be called "complex amplitude". It will be recalled that a complex number is composed of a real part and an imaginary part. It can be represented as a vector in a reference system defined by a real axis and an imaginary axis, which intersect perpendicularly to the point of origin of the vector. The module is the length of the vector, and the argument is the angle that it makes with the real axis.

The Fourier transformation, which can be performed numerically by computer, can provide the complex amplitude associated with each sinusoidal function making up a function. Temporal Fourier transformation is the name used for said transformation applied to a function of time in order to obtain a sum of vibrational components. The pitch of the frequencies (interval between two successive frequencies) of the sinusoidal functions that will appear in the temporal Fourier transform is selected arbitrarily, generally as a compromise between the desired fineness of the results, the duration of the calculation, and if appropriate the capacity limits of the data processing equipment used.

In a preferred embodiment of the invention, we determine, in particular by the temporal Fourier transformation, the spectrum of the vibrational components of each ultrasonic signal received, in other words each of the $N^E \times N^R$ temporal signals mentioned above. The series of frequencies used for all the Fourier transformations is the same. Thus, a complex amplitude associated with each of the $N^E \times N^R$ temporal signals is obtained for each frequency of the series.

For each frequency, this results in $N^E \times N^R$ complex amplitudes, which can be put into the form of a matrix of size $N^E \times N^R$.

Relative to the prior art, which passed directly from the measured signals to mapping by means of a two-dimensional Fourier transform, the invention therefore proposes, at this stage, to go via a one-dimensional Fourier transform, that is, simply temporal, and not spatiotemporal.

It has been found that the energy that is propagated in a medium has a linear behaviour as a function of the frequency. This signifies that the energy associated with a vibrational component in the excitation signal is found again in the vibrational components of identical frequency of the response to said excitation. This feature makes it possible to apply matrix calculation.

If a phase velocity were known, it would be possible to excite all of the emitters at the corresponding frequency in a coordinated manner, in particular in terms of temporal position (phase), so that each emitter starting from the second one reinforces the signal passing in front of it originating from the emitter or emitters located upstream. It would thus be possible on the one hand to amplify the excitation and on the other hand to better observe the response of the medium to this excitation, in particular in terms of energy level.

It was found that matrix calculation made it possible to simulate this investigation and thus accurately locate the velocities of movement of the energy at each frequency in the medium to be characterized.

Matrix calculation teaches an operation called "singular value decomposition" (SVD) applicable to any matrix. According to this mathematical technique, an M×N matrix is decomposed into a certain number of triplets, each comprising a singular value and two associated singular vectors. One of the vectors is of dimension M, the other vector is of dimension N. The number of triplets is equal to the smaller of the two dimensions M and N of the matrix.

On applying this singular value decomposition to each of the aforementioned matrices, each associated with one frequency, for each matrix (each frequency), we obtain $N^E$ triplets comprising an emission vector with $N^E$ complex coordinates, a reception vector with $N^R$ complex coordinates and a singular value, which is a positive real number.

For a given frequency, the $N^E$ emission vectors constitute a base of orthogonal vectors of the mathematical space of the excitations.

The singular value is indicative of the energy level of the modes associated with this frequency.

For each frequency, the $N^E$ singular reception vectors constitute a base of orthogonal vectors in the mathematical space of the responses.

Then we find the plane wave with which the singular reception vectors are associated. A vector is constituted representing a plane wave at each reception point. The coordinates of the vector at a given frequency and at fixed phase velocity are calculated on the basis of the singular reception vectors. Doing this, for each frequency, we examine all the plane waves, by varying the phase velocity.

The square of the sum of the coordinates thus calculated is associated with each value of the pair (frequency, phase velocity). Thus, an image is constituted in grey levels, the values of the level being between 0 and 1. The image thus obtained reveals the curves of phase velocity of the modes that have been propagated along the network of receivers.

In the frequency-propagation velocity reference system, the paths do not all have one and the same energy level, and the level can even vary considerably along a path. Visualization of the real energy levels such as is obtained directly by the prior art of 2DFT lacks clarity in practice, as certain low-energy paths may not appear and even certain medium-energy paths may be masked by the environment of high-energy paths. For this reason, it is advantageous to normalize the representation of the energy levels, for example by giving the value 1 to the maximum level for each frequency.

The proposed solution automatically normalizes the levels represented on the map as the energy levels are expressed in the singular values and the latter, in the preferred solution according to the invention, are eliminated at a certain stage from the calculation of the levels represented by the map.

According to an important feature of the invention, only the frequency responses having the highest energy levels are kept for the mapping. In the embodiment comprising singular value decomposition of the frequency response matrices, filtering of the frequency responses so that only the most energetic are kept can be carried out very simply by only retaining the singular reception vectors associated with a singular value exceeding a certain threshold. For example, for each frequency, only a predetermined number of singular reception vectors, associated with the highest singular values that were found for this frequency, may be retained. As a variant, for each frequency we may only retain the singular reception vectors that are associated with singular values exceeding a certain predetermined threshold, which can be the same for all the frequencies, or can vary according to the frequencies or ranges of frequencies.

This filtering makes it possible to eliminate the low-energy modes from the analysis, as it is considered that they correspond to noise.

The level represented at each point of the image expresses the degree of contribution of a given plane wave to the base of singular reception vectors. The higher it is, the more the vibration mode contributes to the vibrational response.

The quality of the results can be further improved by only retaining the values above a certain predetermined threshold, for example 0.6 or 0.7, in the resultant image. We can choose to represent only the modes with greater contribution, by applying this threshold. All the points that are not retained are for example visualized as if their level were zero.

The high-energy zones are a bit like a mountain range having a ridge that corresponds to a path as defined above. The results can be processed so that only the paths are made to appear.

According to a second aspect of the invention, the device for implementing the aforementioned method, comprising a probe equipped with ultrasonic emission means and a row of ultrasonic receivers, means for activating the means of emission and receiving the signals originating from the receivers in a time window after activation of the means of emission, and processing means for extracting, from the signals received, a map of the energy levels in a frequency-propagation velocity reference system, is characterized in that the means of emission comprise several emitters and the processing means establish the map by mathematically combining the signals received in response to different activation states of the emitters.

As explained above, the different activation states of the emitters can for example mean that, at each time, a single emitter is activated and the others are inactive, the emitter that is activated not being the same from one time to another.

Preferably, the processing means carry out:
the temporal Fourier transform of each signal received by each receiver in response to each activation state, so as to obtain, for each frequency, a matrix $N^E \times N^R$ of the $N^E$ responses acquired by the $N^R$ detectors in response to the $N^E$ activation states,
singular value decomposition of these matrices to extract, from each of them, at least one singular vector forming a component part of a base of the reception space,
calculation of the coordinates of a vector representing a given plane wave in the base of the singular reception vectors.

This will be at the origin of the image supplied as explained above.

Other features and advantages of the invention will also become apparent from the following description, relating to two non-limitative examples of implementation.

DETAILED DESCRIPTION

Figure 1:
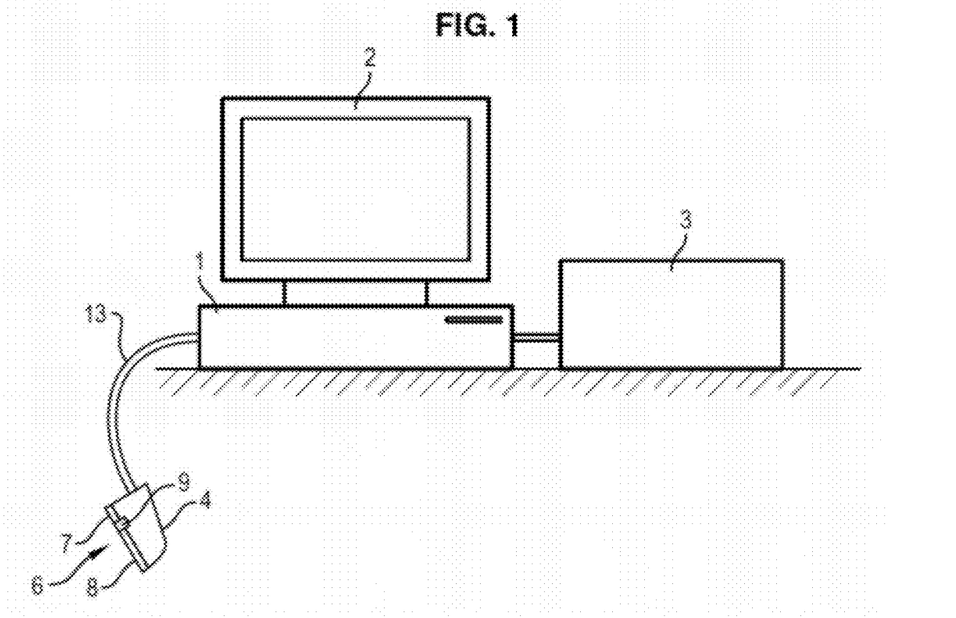
FIG. 1 is a diagrammatic view of a device according to the invention.
Figure 2:
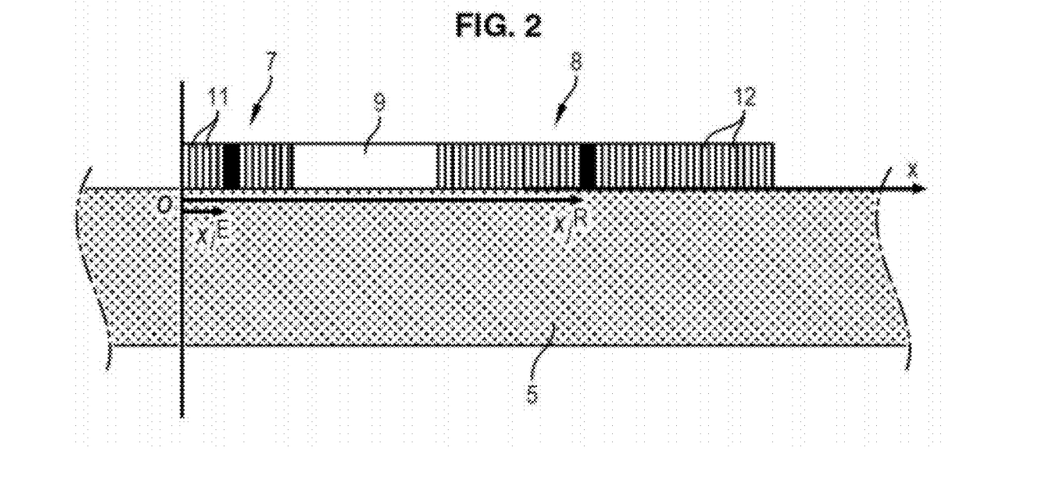
FIG. 2 shows diagrammatically the array of emitters and detectors or receivers of the probe of FIG. 1 applied on a sheet of copper 2 mm thick.

In the example shown in FIGS. 1 and 2 the device according to the invention comprises a processing unit 1 which is connected to a display screen 2 and to a printer 3, as well as to a probe 4.

The probe 4 comprises an active face 6 which is generally of flat shape and which is intended to be applied directly or indirectly on the medium 5 to be characterized. The active face 6 has mainly an emission part 7 and a reception part 8 separated by a barrier 9 preventing direct ultrasonic transmission between the emission part 7 and the reception part 8.

As shown in FIG. 2, the emission part 7 comprises a certain number $N^E$ of emitters 11 and the reception part 8 comprises a certain number $N^R$ of receivers 12. So as not to overload FIG. 2, only a small number of emitters 11 and receivers 12 has been referenced. The emitters 11 are aligned and the receivers 12 are aligned on the same line as the emitters 11. The pitch of the emitters and the receivers is for example 0.8 mm. In the example, this pitch is the same for the emitters and the receivers. However, it may be advantageous to select different pitches, in particular which are not multiples of one another, nor multiples of a common divisor.

The processing unit 1 comprises, in a manner known per se, means for simultaneously triggering the emission of an ultrasonic excitation by the emission part 7 of the probe, time counting, and recording of the signals received at each of the receivers 12 during a predetermined time window starting from triggering of the emission.

Figure 3:
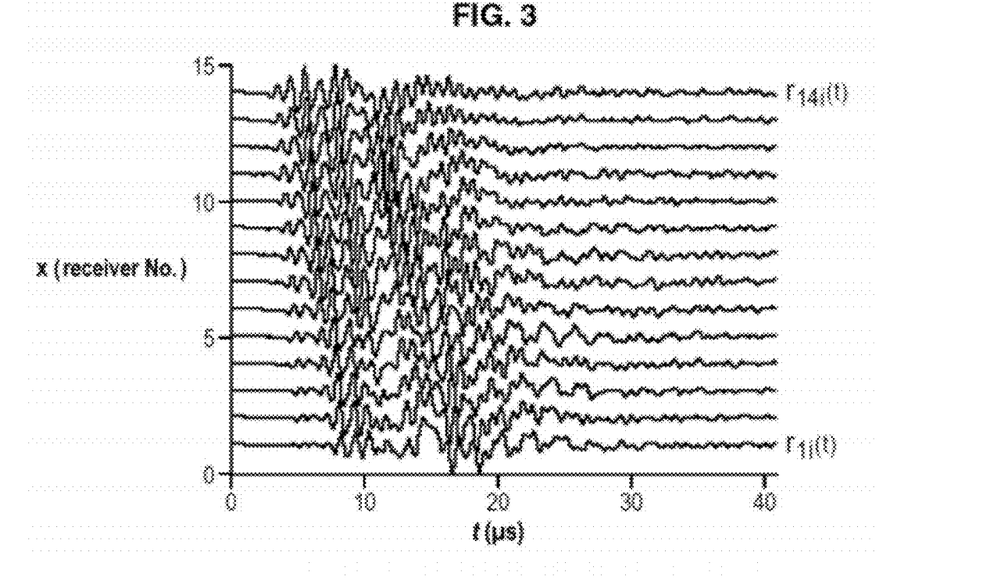
FIG. 3 shows the signals obtained on each of the receivers in response to an excitation signal applied by emitter No. i in the embodiment illustrated in FIG. 2.

FIG. 3 shows the graphical visualization of such a recording during a time window of 40 μs, represented on the abscissa, and for a probe comprising fourteen receivers 12, the numbers of which are shown on the ordinate. For each receiver, the zero level of the signal corresponds to the starting point of the signal associated with this receiver on the vertical ordinate axis.

Each emitter 11 is an ultrasonic transducer which converts an electrical signal received from the processing unit 1 into an ultrasonic signal transmitted to the medium 5 against which the probe is applied. Each receiver 12 is an ultrasonic transducer which converts an ultrasonic signal received from the medium 5 against which the probe is applied into an electrical signal that is sent to the processing unit 1. The processing unit 1 contains means for processing the signals from the reception part 8 of the probe 4 and for extracting from them the variations in phase velocity as a function of the frequency of the ultrasonic waves that have been propagated along the receivers, as will be described in more detail later.

According to the invention, the processing unit 1 is able to generate several activation states of the emission part 7 of probe 4 and to record the signals received by the set of receivers 12 of probe 4 for each of the activation states. The time interval between the generation of two successive states is at least as large as the time window (40 μs in the example in FIG. 3) during which the processing unit 1 records the signals received.

In the example that will be described, each activation state consists of activating just one of the emitters 11, leaving the others inactive. The activation states differ from one another by the number of the emitter that is activated. All the emitters, when they are activated, emit an identical excitation signal, which is typically a response to a Dirac pulse. In this example, the number of activation states is therefore equal to the number $N^E$ of emitters, but this is not limitative.

In the representation in FIG. 2, the x axis is parallel to the direction of alignment of the two emitters 11 and the receivers 12, the subscript "i" represents the number of the emitter 11 under consideration, having a position $x_i^E$ along the x axis, and the subscript "j" represents the number of the receiver 12 under consideration, having a position $x_j^R$ along the x axis.

Thus, for each activation state, the processing unit 1 records $N^R$ spatiotemporal responses forming a set similar to that shown in FIG. 3. Once the processing unit 1 has generated $N^E$ activation states, each corresponding to the activation of one respective emitter 11, the processing unit 1 has acquired $N^E$ sets of $N^R$ spatiotemporal responses, therefore a total of $N^R \times N^E$ spatiotemporal responses. Hereinafter, $r_{ji}(t)$ denotes the spatiotemporal response acquired by detector No. j in response to activation of emitter No. i. Thus, FIG. 3 shows the 14 spatiotemporal responses $r_{1i}(t)$ to $r_{14i}(t)$ following activation of emitter No. i.

The processing of the spatiotemporal responses by the processing unit 1 will now be described.

By temporal Fourier transformation, each temporal signal $r_{ji}(t)$ received by a receiver "j" in response to a state of excitation, in the example the excitation of an emitter "i", is an addition of vibrational components each having a frequency and a complex amplitude, which can be calculated for each frequency from the following formula:

$$R_{ji}(f) = \int_{-\infty}^{+\infty} r_{ji}(t) e^{-i2\pi f t} dt$$

We thus obtain, for each frequency (f), $N^R \times N^E$ complex amplitudes, which can be written in the form of the following matrix R(f) having $N^R$ rows and $N^E$ columns:

$$\begin{pmatrix} R_{11} & R_{12} & \cdots & R_{1N^E} \\ R_{21} & R_{22} & \cdots & R_{2N^E} \\ \cdots & & & \\ R_{N^R 1} & R_{N^R 2} & \cdots & R_{N^R N^E} \end{pmatrix}$$

According to the rules of singular value decomposition, each of the frequency response matrices R(f) can be written in the following form, corresponding to a sum of $N^E$ terms, each of which is a matrix:

$$R(f) = \sum_{n=1}^{N^E} U_n(f) \cdot \sigma_n(f) \cdot {}^t V_n(f)^*$$

Each term of the summation is formed by a vector (column matrix) $U_n(f)$ multiplied by a positive real number $\sigma_n(f)$ multiplied by a row matrix denoted as the transpose of the conjugate of another vector $V_n(f)$.

In this expression, $U_n(f)$ is a so-called "singular" vector with $N^R$ complex coordinates that will be called "reception vector", $V_n(f)$ is a so-called "singular" vector with $N^E$ complex coordinates that will be called "emission vector", and $\sigma_n(f)$ is a singular value. It can be seen that for each frequency f there is a number $N^E$ (the number of activation states, which is equal to the number of emitters in the example) of triplets, each formed from a singular emission vector, a singular reception vector, and a singular value.

It was found according to the invention that the singular emission vectors are each descriptive of a combined excitation of the different emitters, which stimulates a mode of the response, each singular value represents the energy level of the mode associated with the corresponding singular emission vector, and each singular reception vector can be considered as one of the unit vectors of a base of the space of the reception signals. The unit vectors of each base associated with a frequency are orthogonal to one another.

Then a first filtering is carried out, consisting of only retaining the singular vectors that are associated with the highest singular values, corresponding, as has been seen, to the most energetic responses.

Figure 4:
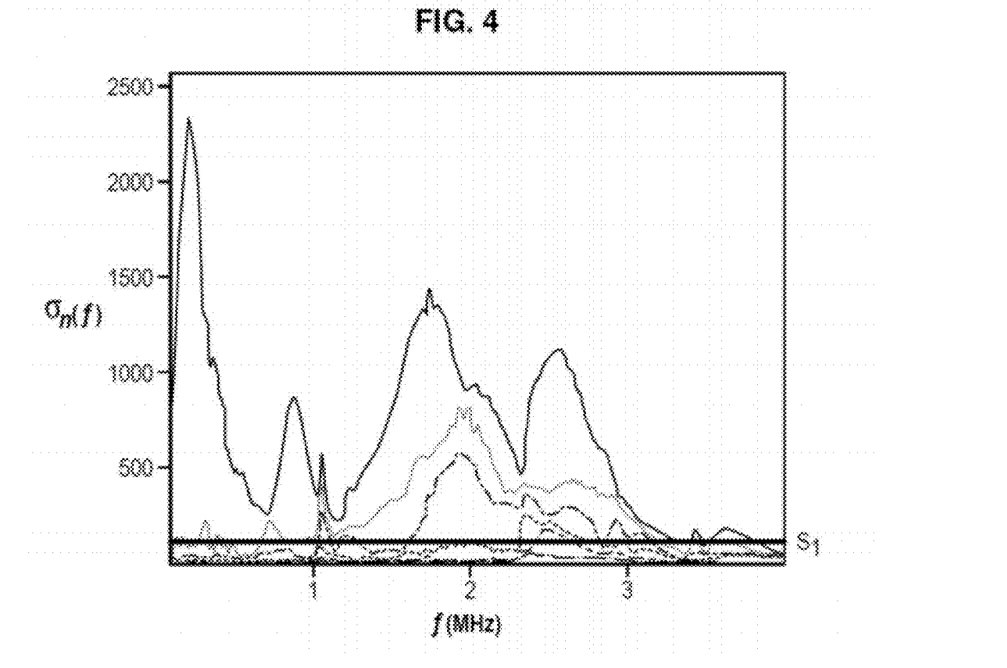
FIG. 4 shows the modules of the singular values as a function of the frequency.

FIG. 4 shows the singular values $\sigma_n(f)$ as a function of the frequency. A threshold $S_1$ is decided arbitrarily. It is considered that the singular values below the threshold $S_1$ are associated with noise phenomena and the corresponding reception vectors are eliminated for the rest of the mathematical processing.

The number of singular values of a matrix is equal to the smaller of its two dimensions. In the example, there are $N^E=8$ emitters and $N^R=14$ receivers, and the smaller of the dimensions of the matrix is therefore $N^E=8$. Therefore for each frequency there are eight singular values. After filtering, we obtain, for each frequency, a reception space having a number $N^{EK}$ of dimensions which is not always the same, which is less than or optionally equal to the number $N^E$ of activation states, and which is less than the number $N^R$ of receivers.

This first filtering could be performed somewhat differently, for example by varying the threshold as a function of the frequency, or by only retaining, for each frequency, a predetermined number of singular values, said number being the same for all the frequencies, or variable as a function of the frequency or by ranges of frequencies. Regardless of which method of filtering is used, for each frequency we obtain a base of $N^{EK}$ singular reception vectors for the waves to be propagated at this frequency along the network of receivers.

Accordingly, it is possible to express any plane wave (associated with a pair frequency f, phase velocity c) in the base associated with this frequency. This wave is expressed by a vector $e^{test}(f,c)$ with $N^R$ coordinates, of which the coordinate of rank j is given by the equation:

$$e^{test}(f, c, j) = \frac{1}{\sqrt{N^R}} \exp\left[i\frac{2\pi f}{c} x_j\right]$$

Division by the square root of $N^R$ is intended to ensure that the sum of the squares of the $N^R$ components, i.e. the module of the vector, is equal to 1.

In the base of the singular reception vectors, the test vector $e^{test}(f,c)$ is expressed as follows:

$$e^{test}(f, c) = \sum_{n=1}^{N^{EK}} \langle e^{test}(f, c) | U_n(f) \rangle U_n$$

Figure 5:
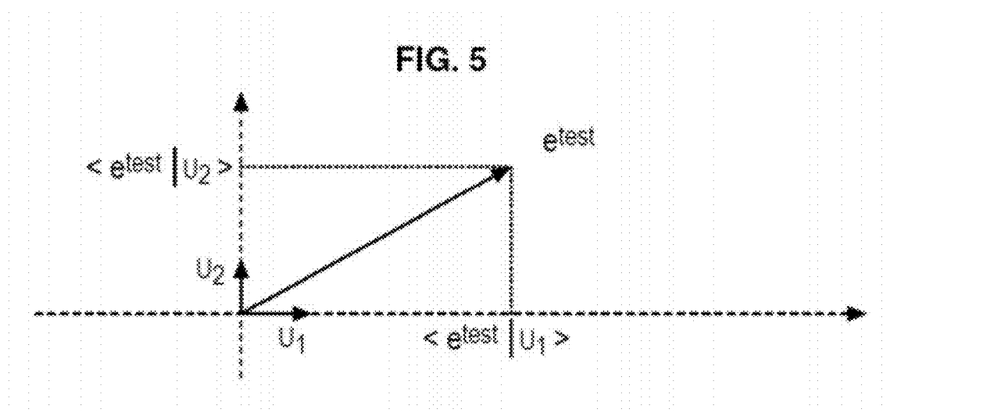
FIG. 5 shows a graph of use of the base of the singular reception vectors.

The notation $\langle \ldots | \ldots \rangle$ indicates a scalar product. FIG. 5 illustrates this operation, consisting of projecting the test vector on the two axes of a base with two dimensions ($N^{EK}=2$).

It is interesting to note that $$\langle e^{test}(f,c) | U_n(f) \rangle = \tilde{U}(f,c)$$

in the above expression $\tilde{U}(f,c)$ is the spatial Fourier transform of the singular vector $U_n$.

In this example, each point (fixed frequency, fixed phase velocity) of the image constructed is defined by:

$$im(f, c) = \sum_{n=1}^{N^{EK}} |\langle e^{test}(f, c) | U_n \rangle|^2$$

It is the square of the module of the projection of the test vector in the base of $N^{EK}$ singular reception vectors that are retained. This is partly arbitrary, we could also, for example, have taken the module itself as the representative value, therefore the square root of the value corresponding to the above formula. As the module of the test vector is equal to 1, the module of its projection in the base of the singular reception vectors retained is always less than or equal to 1. The square of this module is therefore also always less than or equal to 1.

Figure 6:
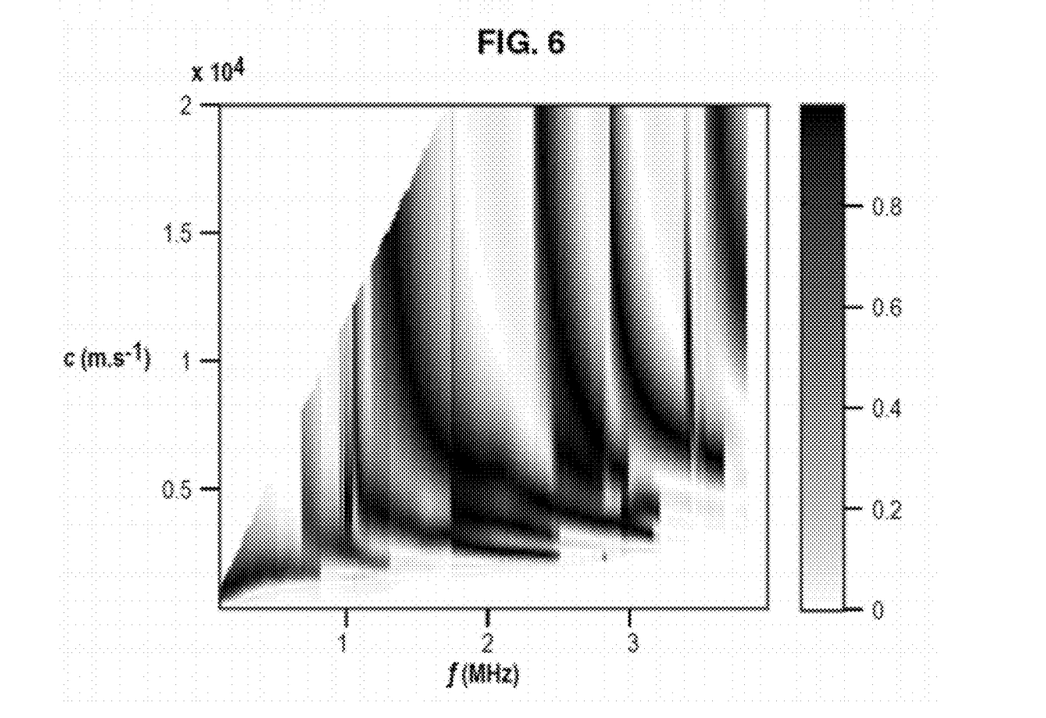
FIG. 6 shows, by grey levels in a frequency-propagation velocity reference system, a map of the module squared of the components of the plane waves in the base of the singular reception vectors, after eliminating the vectors from the base associated with singular values below a fixed threshold.

FIG. 6 shows the image thus obtained, which can be displayed on the screen 2 in FIG. 1, or can be printed graphically by printer 3 in FIG. 1. A scale on the right of the figure explains the value associated with each grey level. The grey levels are between 0 and 1 as the image represents the squared norm of a vector representing a plane wave, and said norm cannot be greater than 1 by construction according to the above disclosure. At the bottom of the figure and on the left of the figure there are two triangular zones that are completely white, corresponding to points that were not calculated as they are of low significance.

Figure 7:
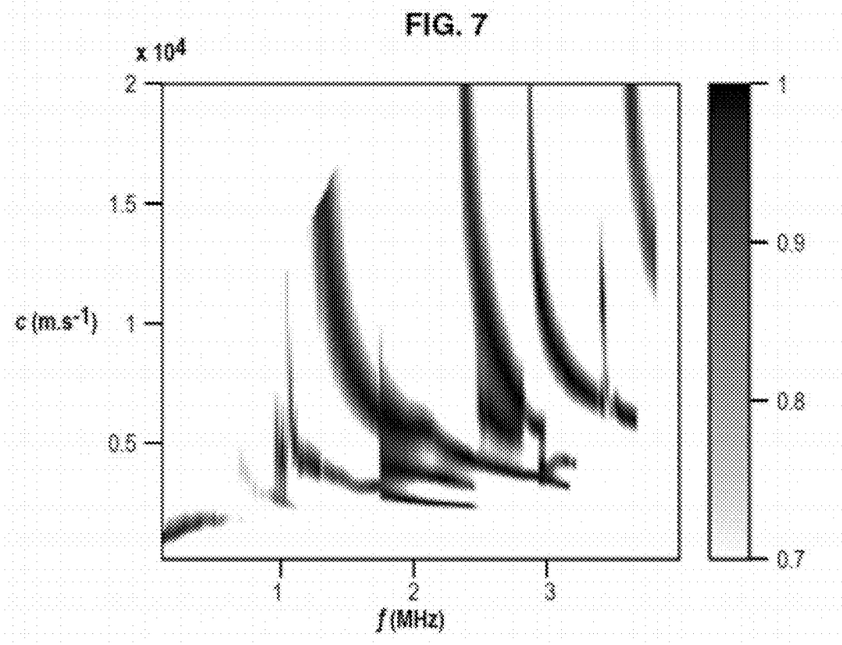
FIG. 7 shows the map from FIG. 6 after only taking into account plane waves such that the associated vector has a squared norm greater than 0.7 in the base of the singular reception vectors.

As shown in FIG. 7, at this stage it is also possible to perform a second filtering, by applying, this time on the resultant image, a second threshold $S_2$ also selected at 0.7 in this example. Then, among the plane waves that contribute to the singular reception vectors, only those are retained that make the greatest contribution (via the highest values of the squared norm of the test vector).

Figure 8:
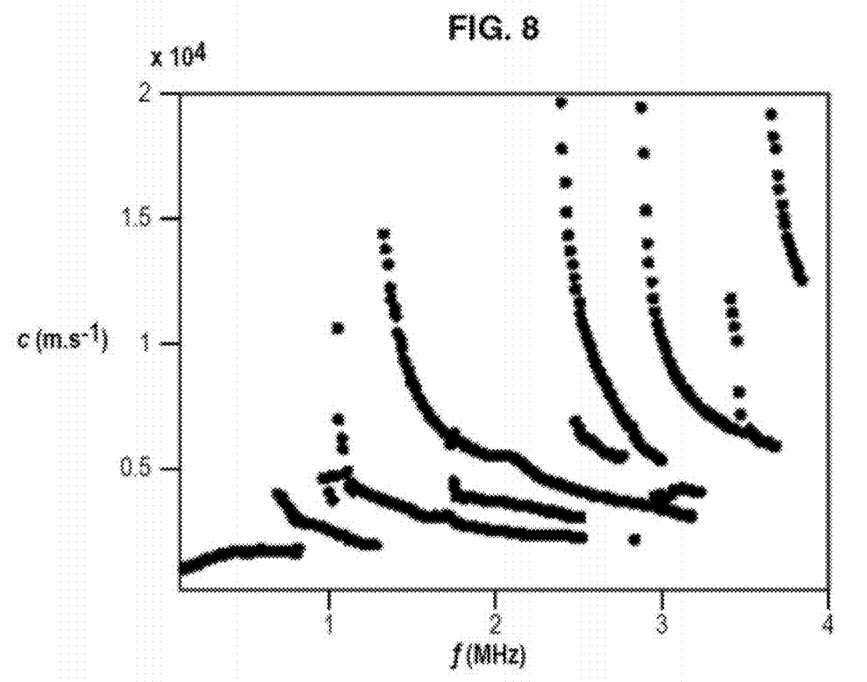
FIG. 8 shows the paths extracted from the map in FIG. 7.

It can be seen from FIG. 7 that the points corresponding to a grey level above the second threshold $S_2$ have a general form of mountain ranges with a ridge. In the representation in FIG. 8, only the ridges were retained, and we thus obtain a representation of the paths such as they were defined above.

Figure 9:
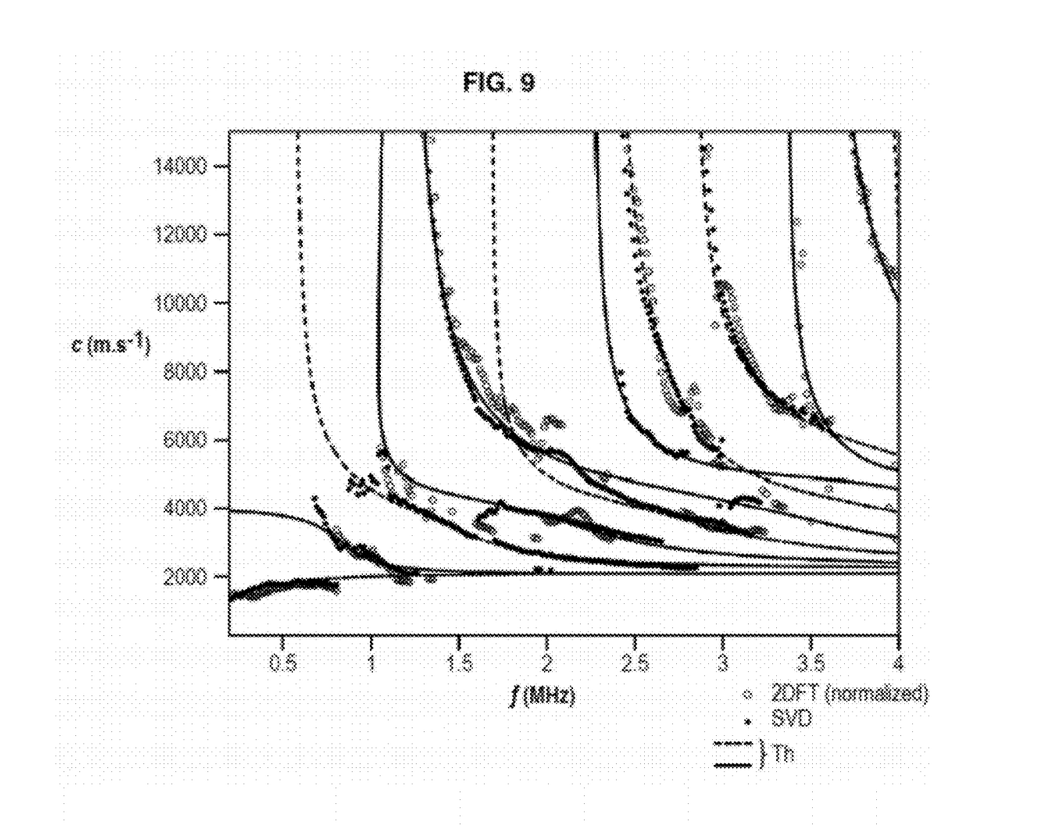
FIG. 9 is a comparative graph of the results obtained with the earlier technology of the bidirectional Fourier transform (2DFT) and with the invention.

In the representation in FIG. 9, the known theoretical paths for a sheet of copper with a thickness of 2 mm are shown with full lines and dotted lines. The paths obtained with the method of the prior art by 2DFT are defined by small circles each representing a point. The paths obtained with the method according to the invention, via singular value decomposition (SVD) are defined by black points. It can be seen on the one hand that the invention reveals paths that are closer to theory, therefore probably more accurate, and on the other hand that the invention reveals a mode that the method of the prior art was unable to detect at all, in the region between 2.5 and 3 MHz.

Figure 10:
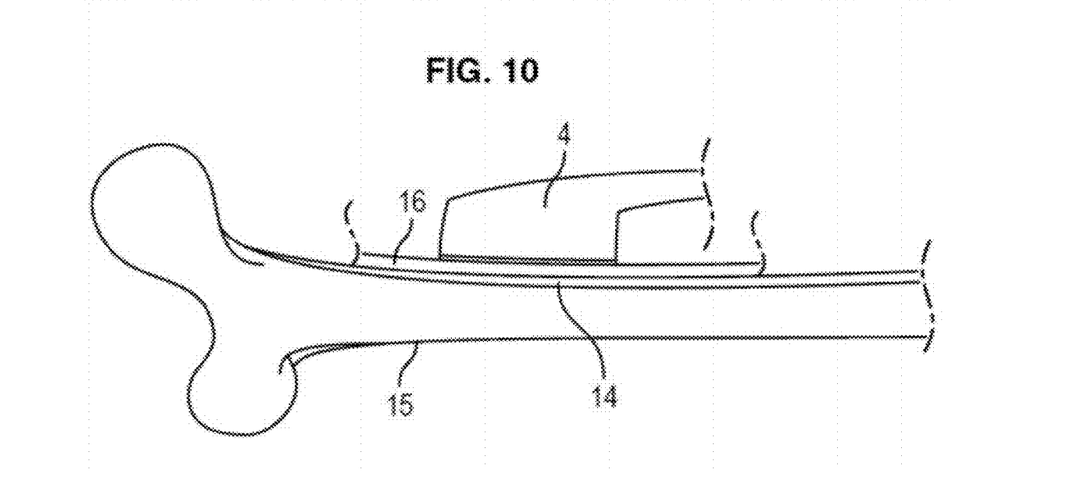
FIG. 10 shows, partially and diagrammatically, application of the probe according to the invention on a patient's arm.

FIG. 10 shows application of the probe 4 on a patient, above the cortical layer 14 of a bone 16 which can be for example a femur, a radius, etc. A certain thickness of soft tissue 16 is interposed between the probe 4 and the external surface of the cortical layer 14.

Figure 11:
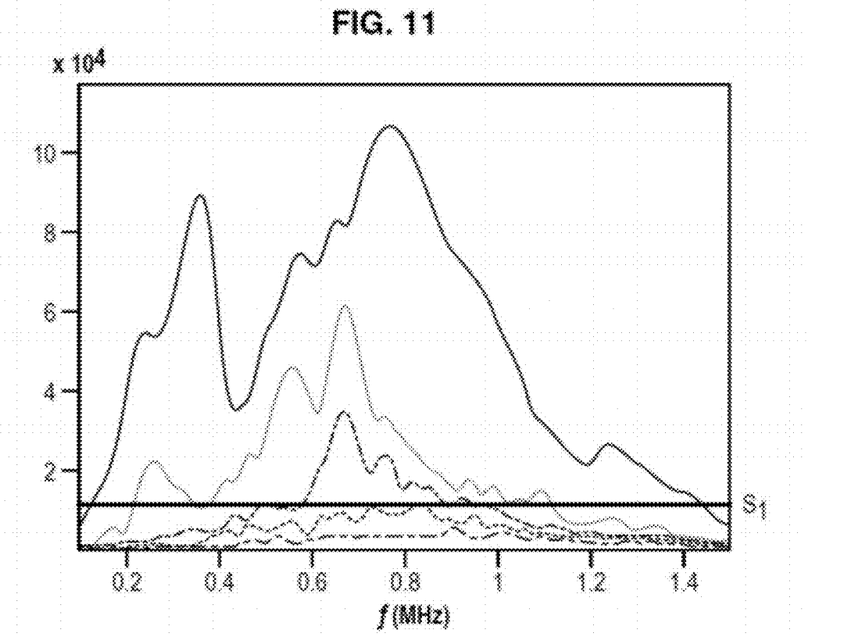
FIG. 11 is a view similar to FIG. 5 but in the case of application of the probe on a radius in vitro.

FIG. 11 shows the singular values obtained as a function of the frequency with a probe with 5 emitters applied directly on a radius during an experiment in vitro. As there are five emitters, there are five singular values for each frequency. The figure also shows an example of constant threshold $S_1$ for all the frequencies. The singular vectors that correspond to singular values that are below this threshold are not retained for the rest of the mathematical processing.

Figure 12:
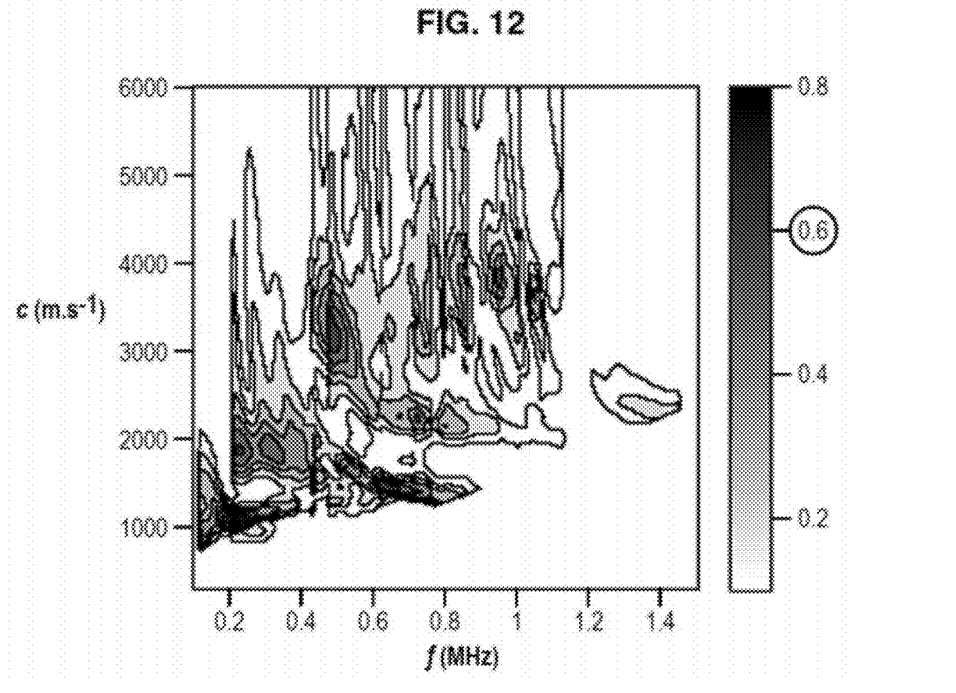
FIG. 12 shows the corresponding map, in which the contour lines of the grey level are shown.

FIG. 12 represents the images obtained after mathematical processing as explained above. On the scale on the right, the grey level equal to 0.6 is circled to indicate that it can be selected as second threshold $S_2$, below which a point is represented as having a grey level equal to zero, much as explained previously with reference to FIG. 7.

Figure 13:
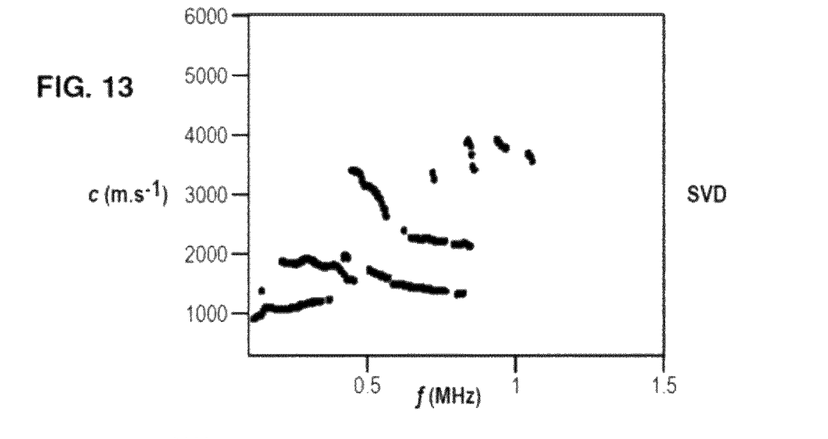
FIG. 13 shows the paths obtained using the technique according to the invention.
Figure 14:
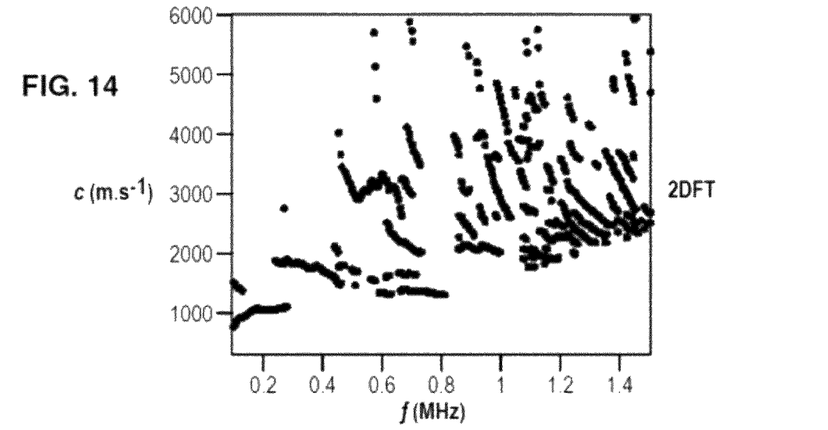
FIG. 14 shows the paths obtained by 2DFT according to the prior art.
Figure 15:
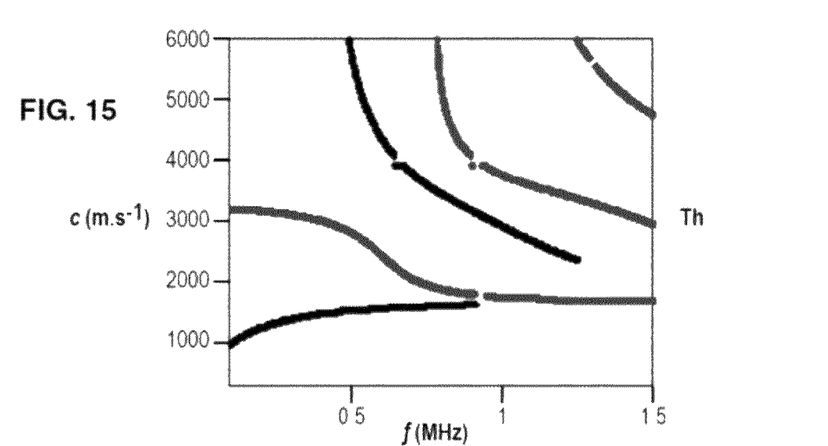
FIG. 15 shows the corresponding theoretical paths.

FIG. 13 shows the paths corresponding to the visualization in FIG. 12. FIG. 14 shows the paths obtained in comparable experimental conditions using the 2DFT method of the prior art. The paths in FIGS. 13 and 14 are to be compared with the theoretical paths in FIG. 15. Whereas the result obtained with the invention (FIG. 13) makes it possible to recognize the theoretical modes, the result obtained with the prior art (FIG. 14) is difficult to use as it is burdened with stray points.

Thus, it is demonstrated that the method according to the invention is able to supply a more accurate result, from which noise has largely been eliminated.

Figure 16:
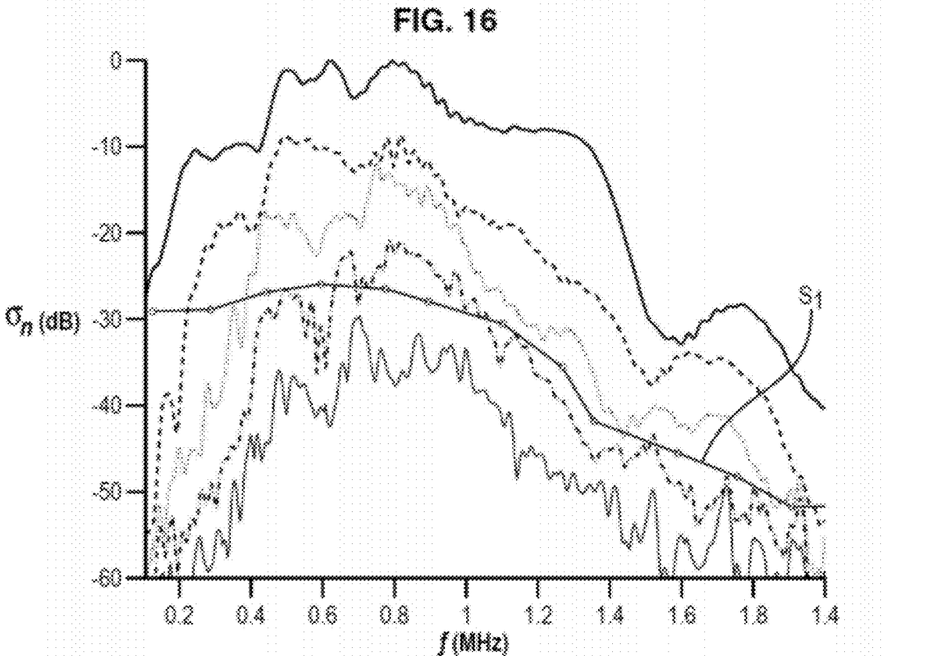
FIG. 16 is a view similar to FIG. 11 but when the invention is applied to a 2 mm thick sheet of a material "imitating" bone, the singular values being indicated in decibels.
Figure 17:
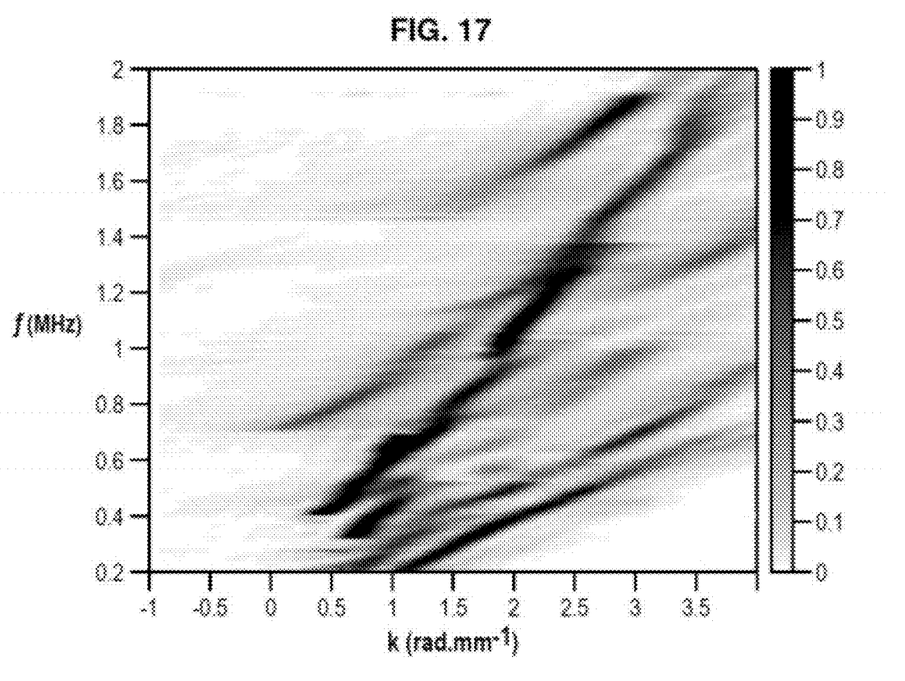
FIG. 17 shows the corresponding map.
Figure 18:
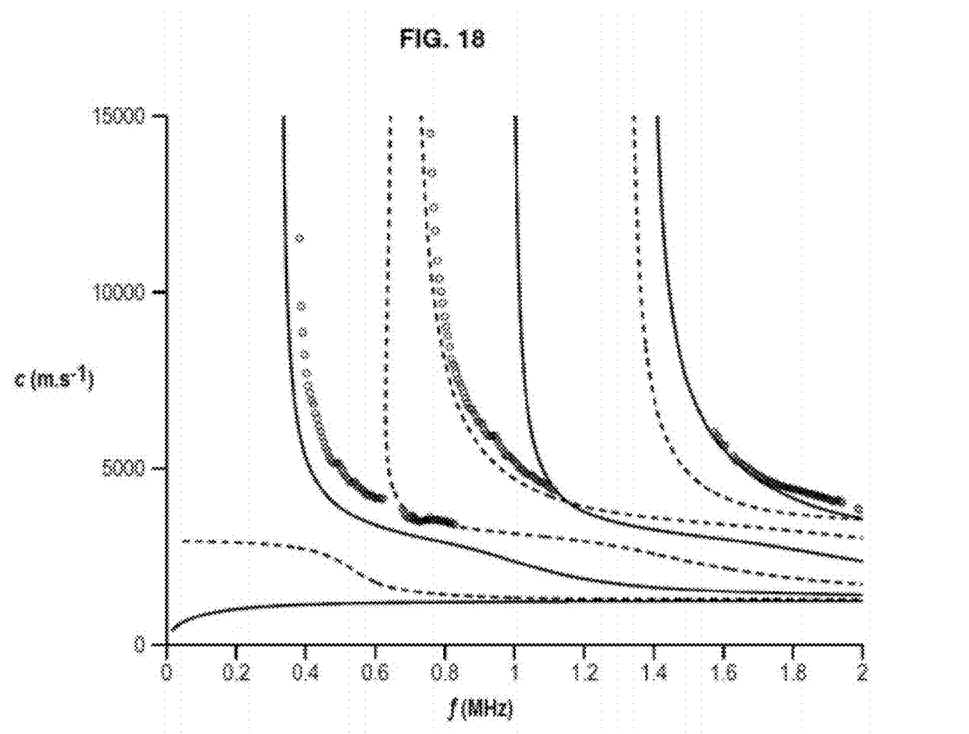
FIG. 18 shows the paths obtained and the theoretical paths of the sheet of material imitating bone.

FIGS. 16 to 18 relate to tests that consisted of implementing the invention on a 2 mm sheet of a material manufactured by Sawbones, a division of Pacific Research Laboratories, Inc., situated at Vashon, Washington State, USA. This synthetic material was developed with the aim of providing physical and mechanical characteristics as close as possible to those of bone.

FIG. 16 shows the singular values as a function of the temporal frequency. The singular values are expressed in decibels of attenuation relative to the value 1 (corresponding to 0 decibel of attenuation). This representation in decibels has the purpose of visualizing low values more clearly than in FIG. 11 for example. Moreover, the threshold S1 chosen is not constant, but varies as a function of the frequency. A threshold determined empirically was associated with frequencies selected with a pitch of for example 0.2 MHz between them. More particularly, the threshold associated with each frequency is selected to be low enough to retain as much useful information as possible but high enough to eliminate noise as far as possible. To do this, the threshold is adjusted, observing the horizontal band corresponding to the frequency considered in the image in FIG. 17, so that this band has as many dark zones as possible, standing out against a light background.

FIG. 17 shows the image, supplied on the screen of the equipment, of the projection of the singular values on the plane of temporal frequency (ordinate)–spatial frequency (abscissa). For a given temporal frequency, the spatial frequency indicates the propagation velocity. In this sense, the graph in FIG. 17 is of the same kind as those in FIGS. 6 and 7, but where the temporal frequency is on the abscissa. In FIG. 17, a vertical scale on the right interprets the grey levels, as explained with reference to FIG. 6.

FIG. 18 shows the phase velocities obtained by the maxima of the image in FIG. 17. The points obtained are represented by small circles. The solid lines and dotted lines illustrate the theoretical paths.

The results obtained for certain paths are reasonably satisfactory, but certain paths and portions of paths are not obtained. The results are less complete than with the sheet of copper. This is not surprising as bone is a medium that is noisier and more attenuating than copper, therefore the signals recorded are of lower quality.

Of course, the invention is not limited to the examples described and shown.

The invention claimed is:

1. An ultrasonic method of characterization of a medium, comprising:
    applying an ultrasonic excitation signal to the medium;
    detecting a response constituted by the ultrasonic signals received at several receiving sites located at different distances from an emission site where the ultrasonic excitation signal was applied; and
    extracting, from the ultrasonic signals received, a map of the modes that have been propagated, in a frequency-propagation velocity reference system,
    wherein for each receiving site, detection is performed successively for at least two different excitation signals, so that at least two responses, whose vibrational components are different and/or are added differently, pass each receiving site,
    wherein a matrix $N^E \times N^R$ of the energy levels and phase differences of the responses for $N^R$ different receiving sites and $N^E$ different emission signals is established for each frequency, thereby generating a matrix of initial frequency responses, and
    wherein the matrix of initial frequency responses is subjected to singular value decomposition, which results for each frequency in a base of singular vectors in the space of the excitations, and a base of singular vectors in the space of the waves that were propagated along the receivers, as well as singular values.

2. The ultrasonic method according to claim 1, wherein the at least two different excitation signals differ by the distance between their respective sites of application and each receiving site.

3. The ultrasonic method according to claim 2, wherein, apart from the distance between the site of application and each receiving site, the at least two excitation signals are roughly identical.

4. The ultrasonic method according to claim 3, wherein the different excitation signals are applied at different points of time, and the responses are detected separately for each excitation signal.

5. The ultrasonic method according to claim 2, wherein the different excitation signals are applied at different points of time, and the responses are detected separately for each excitation signal.

6. The ultrasonic method according to claim 1, wherein the at least two different excitation signals are applied at different points of time, and the at least two responses are detected separately for each of the at least two excitation signals.

7. The ultrasonic method according to claim 1, wherein a spectrum of the vibrational components of each ultrasonic signal received is determined, in particular by calculating a temporal Fourier transform of each signal received.

8. The ultrasonic method according to claim 1, wherein for each frequency, a base of plane waves is expressed in the base of the singular vectors and plane waves that contribute most to the singular reception vectors are designated.

9. The ultrasonic method according to claim 1, wherein, for each frequency, at least one combined emission of the plurality of emitters is determined, for which the response received at the receiving sites is optimized in terms of energy received relative to the energy emitted.

10. The ultrasonic method according to claim 1, wherein several emitters are used and, for each frequency, several combined emissions of several emitters are determined, for which the respective frequency responses are optimized in terms of energy received relative to the energy emitted.

11. The ultrasonic method according to claim 10, wherein a plurality of most energetic frequency responses are selected for determining the plane waves that contribute to the reception signals, and at least one low-energy frequency response is eliminated.

12. The ultrasonic method according to claim 1, wherein the initial frequency responses are normalized.

13. A device for applying a method according to claim 1, comprising:
    a probe equipped with a plurality of ultrasonic emitters and a row of ultrasonic receivers; and a processing unit,
- wherein the processing unit activates the plurality of ultrasonic emitters and receives the signals from the receivers in a time window after activation of the plurality of ultrasonic emitters; and
- wherein the processing unit extracts, from the signals received, a map of the modes that have been propagated, in a frequency-propagation velocity reference system, and
- wherein the processing unit establishes the map by mathematically combining the signals received in response to different activation states of the plurality of emitters.

14. The device according to claim 13, wherein the processing unit carries out:
- the temporal Fourier transform of each signal received by each receiver in response to each activation state, so as to obtain, for each frequency, a matrix $N^E \times N^R$ of the $N^E$ responses acquired by the $N^R$ detectors in response to the $N^E$ activation states,
- singular value decomposition of these matrices for extracting, from each of them, at least one singular vector forming a component part of a base of the reception space,
- calculation of the coordinates of a vector representing a given plane wave in the base of the singular reception vectors.

15. The device according to claim 14, wherein the processing unit eliminates singular vectors corresponding to relatively low energy levels.

* * * * *

UNITED STATES PATENT AND TRADEMARK OFFICE
CERTIFICATE OF CORRECTION

PATENT NO.        : 9,121,810 B2
APPLICATION NO.   : 13/376955
DATED             : September 1, 2015
INVENTOR(S)       : Jean-Gabriel M. Minonzio et al.

Page 1 of 1

It is certified that error appears in the above-identified patent and that said Letters Patent is hereby corrected as shown below:

On the Title page of the Letters Patent, item (73), the Assignee: "Centre Nationale de la Recherche Scientifique – CNRS, Paris (FR)" should read -- Centre National de la Recherche Scientifique (The National Scientific Research Centre), Paris (FR) --; and, Assignee: "Universite Pierre et Marie Curie (Paris 6), Paris (FR)" should read -- L'Universite Pierre et Marie Curie (The Pierre and Marie Curie University), Paris (FR) --

Signed and Sealed this
Twenty-third Day of August, 2016

Michelle K. Lee
*Director of the United States Patent and Trademark Office*